US008618330B2

(12) United States Patent
Snow

(10) Patent No.: US 8,618,330 B2
(45) Date of Patent: Dec. 31, 2013

(54) HEXAFLUORODIMETHYLCARBINOL TERMINATED ALKANE- AND ALKENETHIOLS

(75) Inventor: Arthur W Snow, Alexandria, VA (US)

(73) Assignee: The United States of America, as represented by the Secretary of the Navy, Washington, DC (US)

(*) Notice: Subject to any disclaimer, the term of this patent is extended or adjusted under 35 U.S.C. 154(b) by 680 days.

(21) Appl. No.: 12/549,177

(22) Filed: Aug. 27, 2009

(65) Prior Publication Data

US 2011/0054202 A1 Mar. 3, 2011

(51) Int. Cl.
*C07C 319/00* (2006.01)
*C07C 321/00* (2006.01)
*C07C 323/00* (2006.01)
*C07C 381/00* (2006.01)

(52) U.S. Cl.
USPC ............. 568/65; 568/843; 568/849; 568/62; 568/845

(58) Field of Classification Search
USPC ............................ 568/65, 62, 843, 845, 849
See application file for complete search history.

(56) References Cited

U.S. PATENT DOCUMENTS

| | | | |
|---|---|---|---|
| 6,221,673 | B1 | 4/2001 | Snow et al. |
| 7,189,867 | B1 | 3/2007 | Wynne et al. |
| 7,347,974 | B1 | 3/2008 | Snow et al. |
| 2004/0181023 | A1* | 9/2004 | Yamagishi et al. ........... 526/319 |
| 2005/0124828 | A1* | 6/2005 | Breyta et al. ................. 560/219 |

OTHER PUBLICATIONS

Kobayashi, Y.; Nagai, T.; Kumadaki, I. "Studies on Organic Fluorine Compounds. XLIII. The Ene Reaction of Hexafluoroacetone" Chemical and Pharmaceutical Bulletin, 1984, 32(12), p. 5031-5035.*
W. H. Urry, et al., Multiple multicenter reactions of perfluoro ketones with olefins, *J. Org. Chem.*, 1968, 33 (6), 2302-2310, 2002.
Terrill et al., Monolayers in Three Dimensions: NMR, SAXS, Thermal, and Electron Hopping Studies of Alkanethiol Stabilized Gold Clusters, J. Am. Chem. Soc., 1995, 117 (50), 12537-12548, 2002.
A. W. Snow, et al., Synthesis and Evaluation of Hexafluorodimethylcarbinol Functionalized Polymers as Microsensor Coatings, Journal of Applied Polymer Science, vol. 43, 1659-1671 (1991).
Size-Induced Metal to Semiconductor Snow, et al., Transition in a Stabilized Gold Cluster Ensemble Chem. Mater., 1998, 10 (4), 947-949.
Urquhart, et al., Org. Synth. Coll. vol. III 1955, 363, 1955.

* cited by examiner

*Primary Examiner* — Johann R Richter
*Assistant Examiner* — Amy C Bonaparte
(74) *Attorney, Agent, or Firm* — US Naval Research Laboratory; Joseph T. Grunkemeyer

(57) ABSTRACT

A hexafluorodimethylcarbinol terminated compound, method of making it, and a composition of matter are disclosed. The compound may have the formula $(CF_3)_2C(OH)$-L-M-R. The substructure L may be selected from an optionally substituted propenylene group ($—CH_2CH=CH—$) and trimethylene group ($—CH_2CH_2CH_2—$). The substructure M may be selected from a substituted or unsubstituted methylene chain, a substituted or unsubstituted oxyalkylene chain, and a silicon-containing chain or combination thereof. In one embodiment, M may be selected from $—(CH_2)_n—$, $—(OCH_2CH_2)_m—$, and $—(Si(CH_3)_2O)_p—Si(CH_3)_2—(CH_2)_q—$, wherein n is at least 1, e.g., n is up to 10, m can be at least 1, e.g., m is up to 10, p can be 0 and in one embodiment is from 1 to 10, and wherein q can be 1 and in one embodiment is from 1 to 12. The substructure R represents one of a halogen, $—SH$, $—SZ$, $—S—S—M—L—C(CF_3)_2(OH)$, wherein Z represents a thiol protecting group.

14 Claims, 9 Drawing Sheets

HEXAFLUORODIMETHYLCARBINOL TERMINATED ALKANE- AND ALKENETHIOLS

BACKGROUND

The present disclosure is generally related to a hexafluorodimethylcarbinol terminated thiol compound, to a precursor for forming the compound, to a general synthetic procedure for forming the compound, and to a sensor device which incorporates the compound.

Fluoroalcohol and thiol functional groups confer unique properties on molecular substances, which qualify them for many applications. The unique properties associated with incorporation of the fluoroalcohol functional group include strong hydrogen bonding interaction and proton acidity coupled with a hydrophobic character. This combination of properties makes fluoroalcohol substituted compounds surface active agents in aqueous systems and, as such, they find applications as surfactants, wetting and dispersing agents, defoamers, phase transfer agents, and polymer blend formation promoters, etc. For detection of the organophosphorus chemical warfare agents, the hydrogen bonded interaction of the fluoroalcohol alcohol with the phosphoryl group is advantageous for the sensitivity and selectivity of point sensors in this application. The thiol functional group is beneficial for its coordination with metal ions and for its coordination with neutral metals. As such, the covalently bonded adsorption of thiol functionalized molecules to metal surfaces has been extensively used as a metal surface treatment, and it has found many applications that include nano- and molecular electronics, soft lithography, contact printing, nano-particulate composites, chemical sensing, corrosion resistance, adhesion promotion, and electrochemistry. Numerous ω-functionalized η-alkenethiol compounds have been synthesized and investigated for properties and applications involving metal surfaces.

One particular application is in chemical species detection, which has led to developments of sensor assemblies that include a film of core-ligand material. U.S. Pat. Nos. 6,221,673 and 7,347,974, to Snow, et al., disclose one such chemical sensor assembly, wherein metal or metal alloy nanoparticles are encapsulated by a monomolecular layer of ligand molecules. The ligand molecule has a chain structure with a thiol functional group at one end and a heteroatom functional group at the other end. The thiol group bonds to a metal atom of the nanoparticle surface, and this heteroatom functional group interacts with vapors in the environment. In these disclosures, the heteroatom functional group is a hexafluorodimethylcarbinol structure.

A trifluoromethylcarbinol terminated thiol is disclosed in U.S. Pat. No. 7,189,867 ('867), to Wynne, et al. This compound was designed from the same considerations dating back to use of the hexafluorodimethylcarbinol in polymer coatings for sensor applications described in Snow et al, J. Appl. Poly Sci. 43, 1659 (1991). The '867 patent discloses a molecular agent for monomolecular coatings on metal and metal oxide surfaces. The compound is of general formula $CF_3$—CH(OH)—$CH_2$—$(L)_n$—$CH_2$—SH, wherein L can be a substituted or unsubstituted methylene, a substituted or unsubstituted oxyalkylene, or an alkyl-substituted or unsubstituted siloxanylene. The '867 disclosure includes a synthetic procedure for forming the compound.

BRIEF DESCRIPTION

A first exemplary embodiment of the disclosure is directed toward a compound represented by the formula $(CF_3)_2C$(OH)-L-M-R. In the compound, L is selected from an optionally substituted trimethylene group (—$CH_2CH_2CH_2$—) and an optionally substituted propenylene group (—$CH_2CH$=CH—). M is selected from substituted or unsubstituted methylene, substituted or unsubstituted oxyethylene, and a siloxane chain, and combinations and multiples thereof. R is selected from a halogen, —SH, —SZ, and —S—S-M-L-C$(CF_3)_2$(OH). Z represents a thiol protecting group.

A second exemplary embodiment of the disclosure is directed toward a composition of matter including a metal surface having a group of the general formula $(CF_3)_2C$(OH)-L-M-S— bonded thereto, in which L and M are substructures as defined above.

Another embodiment of the disclosure relates to a method of forming a hexafluorodimethylcarbinol terminated thiol compound, which includes (1) reacting a ω-halo-α-olefin with hexafluoroacetone to form a first intermediate; (2) optionally hydrogenating a double bond of the first intermediate to form a second intermediate; and (3) transforming the first or second intermediate by first reacting it with thiourea followed by base hydrolysis to form the compound.

Another exemplary embodiment of the disclosure is directed toward an encapsulated particle comprising a hexafluorodimethylcarbinol terminated thiol compound. Such particle finds use as a vapor responsive electronic transducer in a chemical sensor.

DETAILED DESCRIPTION

Figure 1:
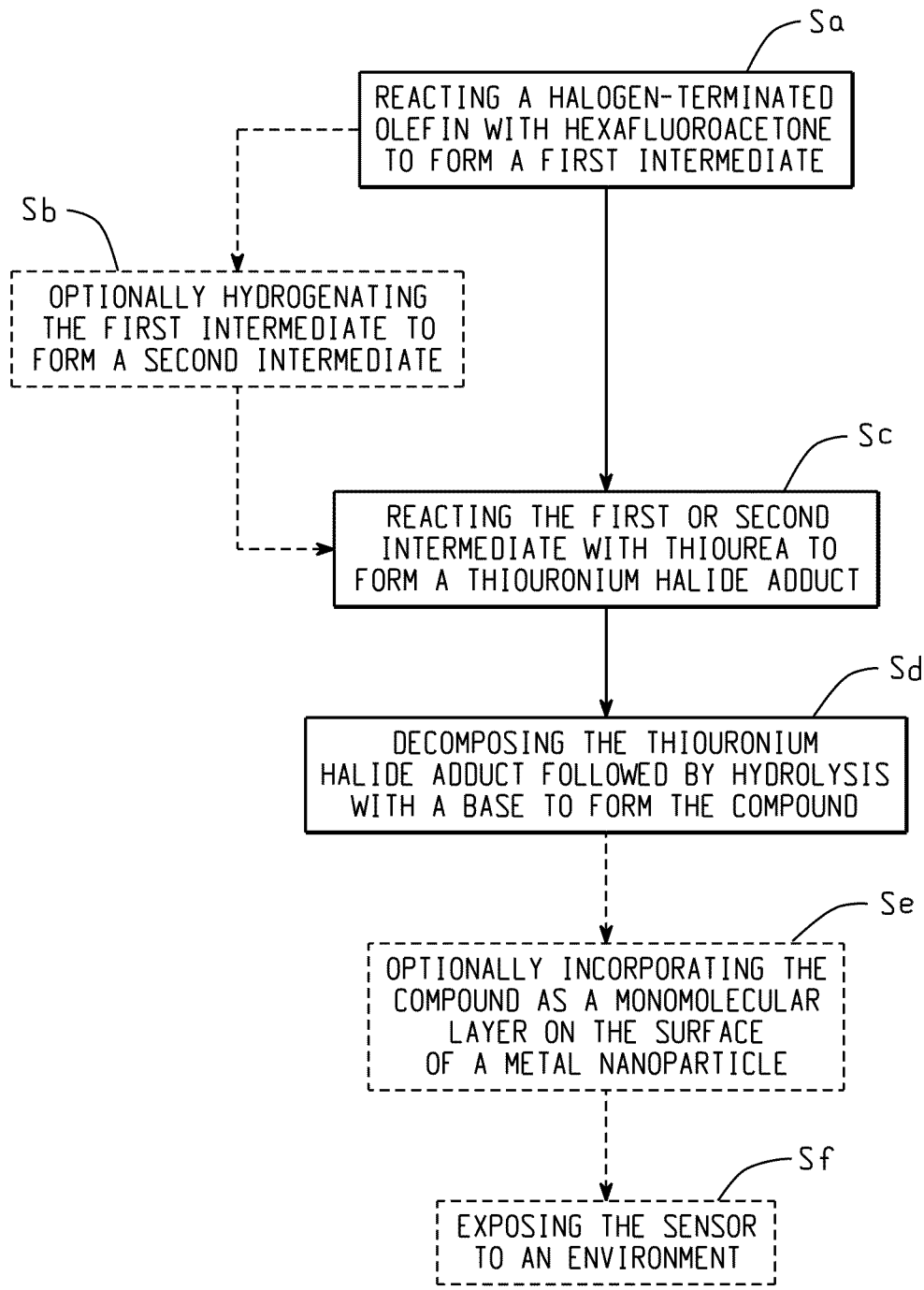
FIG. 1 is flow chart showing a method of producing a hexafluorodimethylcarbinol terminated thiol compound according to one embodiment of the present disclosure.

One aspect of the present disclosure is directed toward a hexafluorodimethylcarbinol terminated compound ("the compound"). In one embodiment, the compound includes a hexafluorodimethylcarbinol functionality and a thiol functionality (or a precursor therefor), which are connected by a chain. A chain, as used herein, is a series of (at least three) linked atoms, wherein the hexafluorodimethylcarbinol moiety and the thiol group are linked to different atoms that are both part of the same chain. The present disclosure is also directed toward a compound having specific application in coatings for chemiresistor sensors. In some aspects, the compound includes functionalities of the types that either bond to the metal nanoparticles surface of a sensor or interact with targeted chemical vapors to be detected.

The disclosure is directed to compounds having a hexafluorodimethylcarbinol functional group at a first end of a molecular chain and a thiol group (or a precursor for the thiol group) at a second end. The molecular chain can be a substituted or unsubstituted hydrocarbon chain, which can be saturated or unsaturated, a substituted or unsubstituted oxyalkylene chain, an alkyl-substituted or unsubstituted silicon-containing chain, or a combination thereof. The molecular chain can be of variable length. However, in one embodiment the molecular chain is up to 18 carbon atoms in length (or, where the chain includes heteroatoms selected from Si and O, no greater than 18 atoms in length). For some applications, such as certain sensor applications, the molecular chain may be no greater than 13 carbons or linked atoms in length. In some cases, a resistance of a coating formed of compounds of longer chains may be too high. Longer chains (i.e., thicker shells) tend to correlate with too low conductivity. (see, U.S. Pat. No. 6,221,673 ("673") and U.S. Pat. No. 7,347,974 ("974"), to Snow, et al., the disclosures of which are incorporated herein in their entirety by reference; see also, "Metal-Insulator-Metal Ensemble Gold Nanocluster Vapor Sensors", in Defense Applications of Nanomaterials, Miziolek, et al., Eds., American Chemical Society Symposium Ser. No. 891, Washington, 2004, Ch. 3). In one embodiment, the chain has no fewer than three carbons. Chains of shorter lengths tend not to stabilize as efficiently. Sensors coated with compounds having shorter length chains (i.e., thinner shells) tend to short electrically. For example, thin spots in a monolayer of the compound can cause adjacent metal nanoparticles of the sensor to contact and fuse thereby bypassing the monolayer's modulation of electrical resistance and shorting the sensor. These thinner shells also tend to correlate with instability toward agglomeration.

As used herein, a silicon-containing chain is an optionally substituted chain comprising at least one silicon atom which is spaced from the terminal thiol group or thiol precursor by at least one carbon atom, the silicon-containing chain being free of Si to Si bonds. Such a chain is exemplified by substituted and unsubstituted siloxanes and silanes, which are alkyl terminated, at the thiol end of the molecule. In one embodiment, the silicon-containing chain is linked to the thiol or thiol precursor by an alkyl group of up to 5 carbons in length.

As used herein a thiol precursor includes a group which can react or decompose to form a thiol or sulfur terminated ligand.

As used herein, "substituted" means that at least one hydrogen connected with the molecular chain is substituted with a substituent, such as an alkyl, alkenyl, alkoxy, halo or hydroxyl group, or combination thereof, which substituent may be shorter, in length than the molecular chain, e.g., from 1-6 carbons in length.

The following exemplary carbon-containing chains can be situated between the thiol group and the hexafluorodimethylcarbinol group: a linear alkyl group; a branched alkyl group; a saturated alkyl group; an unsaturated alkyl group; a branched cyclic alkane; a branched cyclic alkene; a substituted chain; an unsubstituted chain; and, a combination thereof. In one embodiment, the carbon containing chain can contain one or more heteroatoms, such as, Si and/or O, and may include, for example, an alkyl-substituted or unsubstituted chain which includes silicon, a substituted or unsubstituted oxyalkylene, and combinations thereof.

The compound may have a general structure which can be represented as follows: $(CF_3)_2C(OH)$-L-M-R. The substructure L may be selected from a propenylene group ($—CH_2CH=CH—$), a trimethylene group ($—CH_2CH_2CH_2—$), which can be substituted or unsubstituted, and combinations thereof. The substructure M may be selected from a substituted or unsubstituted methylene chain, a substituted or unsubstituted oxyalkylene chain, and an alkyl-substituted or unsubstituted silicon-containing chain, and combinations and multiples thereof. In one embodiment, M may be selected from $—(CH_2)_n—$, $—(OCH_2CH_2)_m—$, and $—(Si(CH_3)_2O)_p—Si(CH_3)_2—(CH_2)_q—$, and combinations thereof. The substructure R may represent a thiol group or a precursor therefor, which is capable of being converted to a thiol group by reaction or substitution. R can be selected from a halogen, $—SH$, $—SZ$, and $—S—S-M-L-C(CF_3)_2$ $(OH)$, wherein Z represents a thiol protecting group. In particular, the compound can be derivatized as the disulfide or with a well-known thiol protecting group, in which case Z can be selected from $—COCH_3$, $—COCF_3$, $—COC(C_6H_5)_3$, $—C(CH_3)_3$, $—C(C_6H_5)_3$, $—CH(C_6H_5)_2$, and $—CH(C_6H_5)$. n, m, and p may each assume integer values of at least 0, providing that the chain represented by $—C-L-M-$ is at least three atoms in length, and in one embodiment wherein the L moiety is at least 3 atoms in length.

In one embodiment, n is at least 1. In one embodiment, n is up to 16, and in another embodiment, up to 10. In one embodiment, n is up to 5. In one embodiment, n is 1 or 2. In one embodiment, m is at least 1. In one embodiment, m is up to 10. In one embodiment, m is up to 4. In one embodiment, m is 1. In one embodiment, p is at least 1. In one embodiment, p is up to 10. In another embodiment, p is up to 5. In one embodiment, p is 1. In one embodiment, q is at least 1. In one embodiment, q is up to 12. In one embodiment, q is 1-3. In another embodiment, q is at least 3. In one embodiment, q is 1. In one embodiment, q is 3.

In one exemplary embodiment, the compound is of the structure $(CF_3)_2C(OH)—CH_2CH_2CH_2—(CH_2)_n—SH$, where n is as described above. In another embodiment, the compound is of the structure $(CF_3)_2C(OH)—CH_2CH=CH—(CH_2)_n—SH$, where n is as described above. In another embodiment, M is $—(OCH_2CH_2)_m—$, where m is at least 1. In another embodiment, M is $—(Si(CH_3)_2O)_p—Si(CH_3)_2—(CH_2)_q—$, where p is at least 0 and q is at least 1. In one embodiment, q is at least 3. In one embodiment, q is 3. In one embodiment, R is $—SH$. In another embodiment, R is bromine.

FIG. 1 shows a general synthetic procedure for forming the compound. Generally, a starting compound comprising a terminal (a) olefin and having the general structure $CH_2=CH—CH_2-M-X$ is reacted with hexafluoroacetone (step a). In one embodiment, the substructure X can be a halogen. The substructure M represents a carbon-containing molecular chain as described above, comprising entirely carbon atoms or in which one or more of the carbon atoms may be replaced by a heteroatom selected from Si and O and where the carbons in the chain may be substituted or unsubstituted. The carbon-containing molecular chain can include, for example, a substituted or unsubstituted methylene, a substituted or unsubstituted oxyalkylene, an alkyl-substituted or unsubstituted silicon-containing group, and combinations thereof. Some embodiments employ a four or five carbon chain. In one embodiment, the starting compound has no more than 13 carbons in the main chain linking X with the terminal C═C. The synthesis is considered general to a range of alkane or alkene chain lengths, as well as for the substitutions of other types of foregoing chains. The electrophilic addition of the hexafluoroacetone with the terminal olefin forms a first intermediate having the formula $(CF_3)_2C(OH)-CH_2-CH=CH-M-X$, wherein the double bond shifts one unit from the initial olefin end of the chain, and the hexafluorodimethylcarbinol functionality links to the terminal carbon. This first intermediate is optionally hydrogenated (step b) to form a second (alkane) intermediate (fully saturated chain) of the formula $(CF_3)_2C(OH)-CH_2-CH_2-CH_2-M-X$. The substructure X of the first or second (e.g., alkane or alkene) intermediate is displaced by thiourea, and a thiouronium adduct is formed (step c). The thiouronium adduct is hydrolyzed by a base (step d) to form the product compound.

As a specific example, the following exemplary synthesis illustrates the process using a halogen terminated terminal alkene (structure 1) as the starting compound. The exemplary synthesis employs an alkene chain having five carbons. The carbon-carbon double bond is situated at the olefin end of the chain, where it can undergo electrophilic addition of hexafluoroacetone. The halogen group is situated at the opposite end of the molecular chain. A bromine atom is the halogen utilized in the exemplary synthesis.

usually present as a mixture of both cis and trans isomers, but may also be exclusively cis or trans.

A second synthesis is described for preparation of a hexafluorodimethylcarbinol terminated alkanethiol. This procedure is the same as described above except that a step b is added. This second synthesis is described below using the foregoing 5-carbon ω-bromo-α-olefin, 5-bromopent-1-ene (structure 1). The first step a of the synthesis is the same as the foregoing procedure resulting in structure 2: the electrophilic addition of hexafluoroacetone to structure 1, which forms the adduct $(CF_3)_2C(OH)-CH_2-CH=CH-CH_2-CH_2-Br$ shown as structure 2. The next step b includes hydrogenation of the bromoalkene intermediate 2 to form a corresponding bromoalkane intermediate $(CF_3)_2C(OH)-(CH_2)_5-Br$ of structure 3. The third step c and fourth step d include conversion of the bromoalkane intermediate to the alkanethiol product of structure 5. These steps are analogous to steps c and d described above.

While the method and other methods of the disclosure are illustrated as a series of steps, it will be appreciated that the various methods of the disclosure are not limited by the illustrated starting materials or the illustrated sequences of such steps. In this regard, it is to be appreciated that the synthesis can be performed utilizing any of a variety of starting materials, wherein the X substituent can be any functionality that is capable of being replaced by a thiol group or

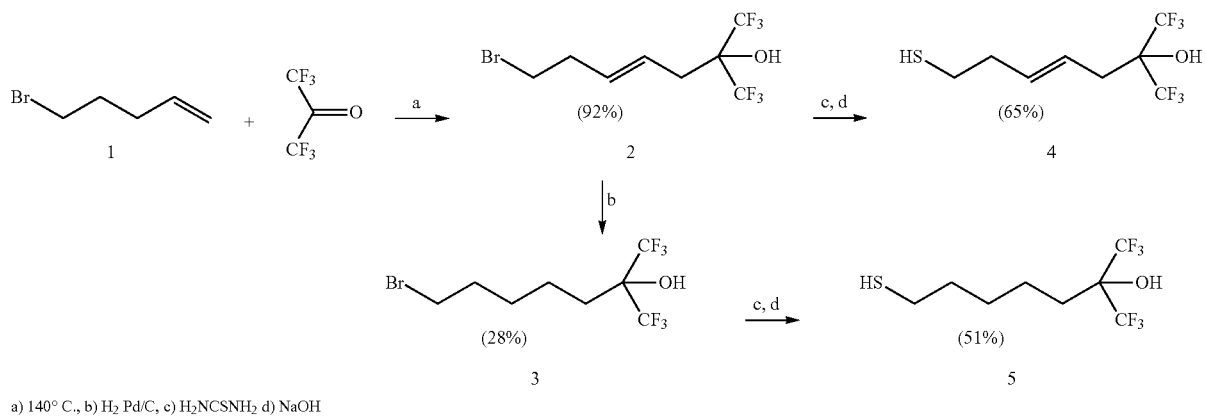

a) 140° C., b) H$_2$ Pd/C, c) H$_2$NCSNH$_2$ d) NaOH

A first synthesis is described for production of a hexafluorodimethylcarbinol terminated alkenethiol (compound 4). In particular, the first step a of the synthesis is the electrophilic addition of hexafluoroacetone with a ω-halo-α-olefin as the starting compound having the formula $CH_2=CH-CH_2-CH_2-CH_2-X$, where X is a halogen (e.g., Br). This step a may be performed using the procedure described in Urry, et al., *J. Org. Chem.* 1968, 33, 2302. In the above reaction, structure 1 (5-bromopent-1-ene) forms the adduct $(CF_3)_2C(OH)-CH_2-CH=CH-CH_2-CH_2-Br$, shown as structure 2. This addition causes the double bond to shift one unit from the initial olefin end of the chain. The double bond in structure 2 may be cis, trans, or a mixture of the two isomers. The alkylbromide is then converted to a thiol (step c) by reaction with thiourea and subsequent base hydrolysis (step d). This reaction may be performed using the procedure outlined in Urquhart, et al., Org. Synth. Coll. Vol. III 1955, 363. Thiourea displaces the bromide substituent to form a thiouronium bromide adduct (step c), which is not isolated but hydrolyzed by addition of a base (step d) to form the product of structure 4. The double bond in the resultant product is protected thiol group. Some steps may occur in different orders and/or concurrently with other steps apart from those illustrated and described herein, in accordance with the disclosure. It is further noted that not all illustrated steps may be required to form the compound of the present disclosure. The methods of the disclosure, moreover, may be implemented in association with the disclosed starting materials, as well as with other starting materials not illustrated or described, wherein all such alternatives are contemplated as falling within the scope of the disclosure and the appended claims.

In structure 4, the double bond positioned beta to the hexafluorodimethyl carbinol group is relatively unreactive due to electronic induction and steric effects. The individual steps of the present disclosed syntheses (referenced above as steps "a", "b", "c", and "d") provide excellent yields; they may be conducted on multigram or larger scales. The presence of the double bond in the alkenethiol product of structure 4 does not cause a significant difference in properties between compounds 4 and 5, so the somewhat lower yield for the hydrogenation step b of the second synthesis can be avoided by forming the alkenethiol product of structure 4 in place of the alkanethiol product of structure 5.

The electrophilic addition a of hexafluoroacetone to the terminal olefin can be performed under temperature conditions in a range between 25° C. and 210° C., depending on the olefin reactivity. Additions at higher temperatures tend to cause byproducts because the reaction occurs too fast. Additions at lower temperatures can cause the reaction to occur too slowly. In one embodiment, the electrophilic addition occurs at a temperature between 130° C. and 140° C.

The hydrogenation step b that converts the first (alkene) intermediate 2 to the second (alkane) intermediate 3 is performed in one embodiment utilizing a palladium and/or a platinum catalyst on a carbon carrier. Other embodiments can utilize either the platinum and/or the palladium catalyst on other carrier materials. These catalysts can be loaded up to 2%, 5% and 10% by weight of the carrier. The embodiment disclosed herein utilized a 10% loaded carrier to achieve the hydrogenation step b.

It is more generally noted that a first step of the present synthesis can utilize, as structure 1, any halogen-terminated alkene, wherein the halogen is selected from fluorine, bromine, chlorine, iodine, and combinations thereof. Bromide is utilized in one embodiment because an alkene compound having a terminal bromine atom is relatively inexpensive and it exhibits properties that provide higher yields in synthesis procedures.

The hexafluorodimethylcarbinol terminated thiol compounds can be incorporated as a self-assembled monomolecular layer on the surfaces of metal nanoparticles (shown as step e in FIG. 1). By monomolecular, it is meant that the layer has a thickness approximately equivalent to that of the length of a single molecule of the exemplary compound. By self-assembled, it is meant that the compound bonds to the metal surface by way of the sulfur atom with the hexafluorodimethylcarbinol functionality oriented outermost in the layer. By nanoparticle, it is meant a particle which is less than 1000 nanometers in maximum diameter, and generally less than 100 nanometers in maximum diameter. The nanoparticle may be generally spherical in shape or have another shape, such as an ovoid, rod, plate, spike, or the like, or it can be attached to other particles. The nanoparticle generally includes metal atoms, the metal atoms being present at the surface of the nanoparticle core or forming the entire nanoparticle. In one embodiment, the nanoparticle is formed in major part, e.g., at least 90% by weight, of metal. The metal may include an electrically conductive metal, such as gold. As will be appreciated, while in some embodiments, the exemplary compound may provide 100% by weight of the layer surrounding the nanoparticle, it is also contemplated that the compound may be mixed with other self assembling compounds to form the layer, in which case, the exemplary compound may comprise at least 50 mol. % of the layer.

In the exemplary embodiment, the sulfur atom of the compound covalently or otherwise binds to metal atoms of the nanoparticle surface, and the thiol hydrogen may be given off or it may remain associated with the sulfur atom of the compound. As used herein, an S— group bound to a metal surface is defined as including both a presence and an absence of the thiol hydrogen. If the compound is a disulfide, the disulfide bond is broken and each sulfur is individually bonded to the metal.

The hexafluorodimethylcarbinol terminated thiol compounds can be incorporated as a self-assembled monomolecular layer on the surfaces of metal nanoparticles. Assemblies of such treated metal nanoparticles are referred to herein as ligand-stabilized metal nanoclusters. The thiol monomolecular layer may be referred to as a ligand shell and the metal nanoparticle as a core. The '673 and '974 patents disclose suitable conductive metals which may be utilized in the present nanoparticles, such disclosures of which are incorporated herein by reference in their entireties. In one embodiment, the metal core includes gold, due to its stability toward surface oxidation. A film composed of an assembly of these ligand-stabilized metal nanoparticles ("nanoclusters") can be used as a transducer for chemical sensing. Sensors comprising the exemplary ligand-stabilized metal nanoparticles can be formed according to the methods disclosed, for example in Wohltjen, et al., *Anal. Chem.* 1998, 70, 2856 and in the '673 patent.

For example, nanoparticles of gold or other metals or alloys of 0.8-40 nm in maximum dimension can be encased in a ligand shell comprised of the exemplary compound (5) of, for example, about 0.4-10 nm in thickness. The magnitude of electron transport through such a film of encapsulated gold nanoclusters can be dependent on the dimensions of the gold core and on the thickness of the monolayer shell (Terrill, et al., *J. Am. Chem. Soc.* 1995, 117, 12537; Snow, et al., *Chem. Mater.* 1998, 10, 947). The thickness of the encapsulating monomolecular layer including the exemplary hexafluorodimethylcarbinol terminated thiol compound around a nanometer-sized gold nanoparticle or cluster can be sufficient to allow a small amount of current to pass through adjacent clusters, while at the same time being highly modulated by the fluoroalcohol induced adsorption of a chemical analyte.

Figure 2:
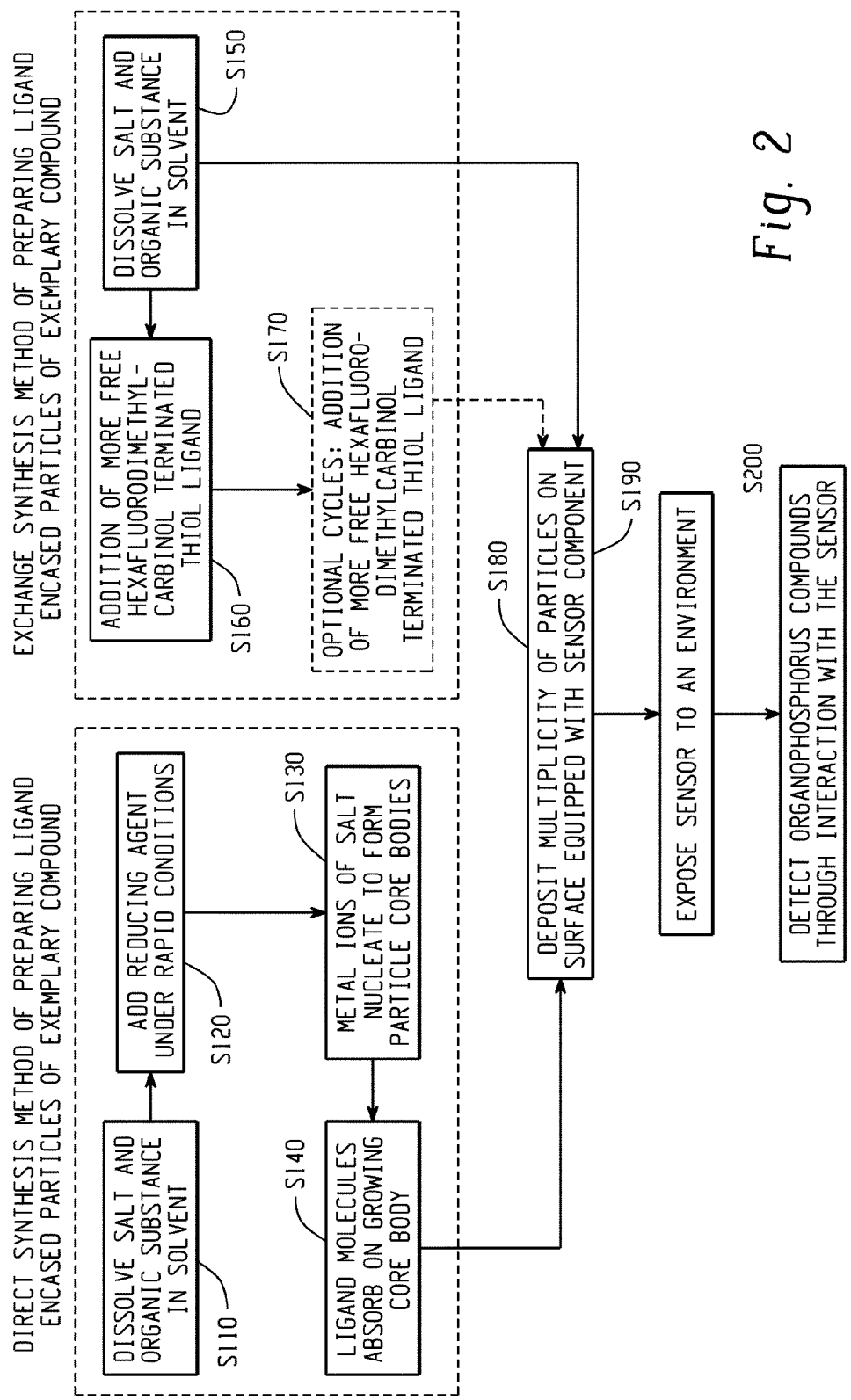
FIG. 2 is a flow chart showing a method of forming the exemplary compound and detecting an organophosphorus compound with the exemplary compound.
Figure 3A:
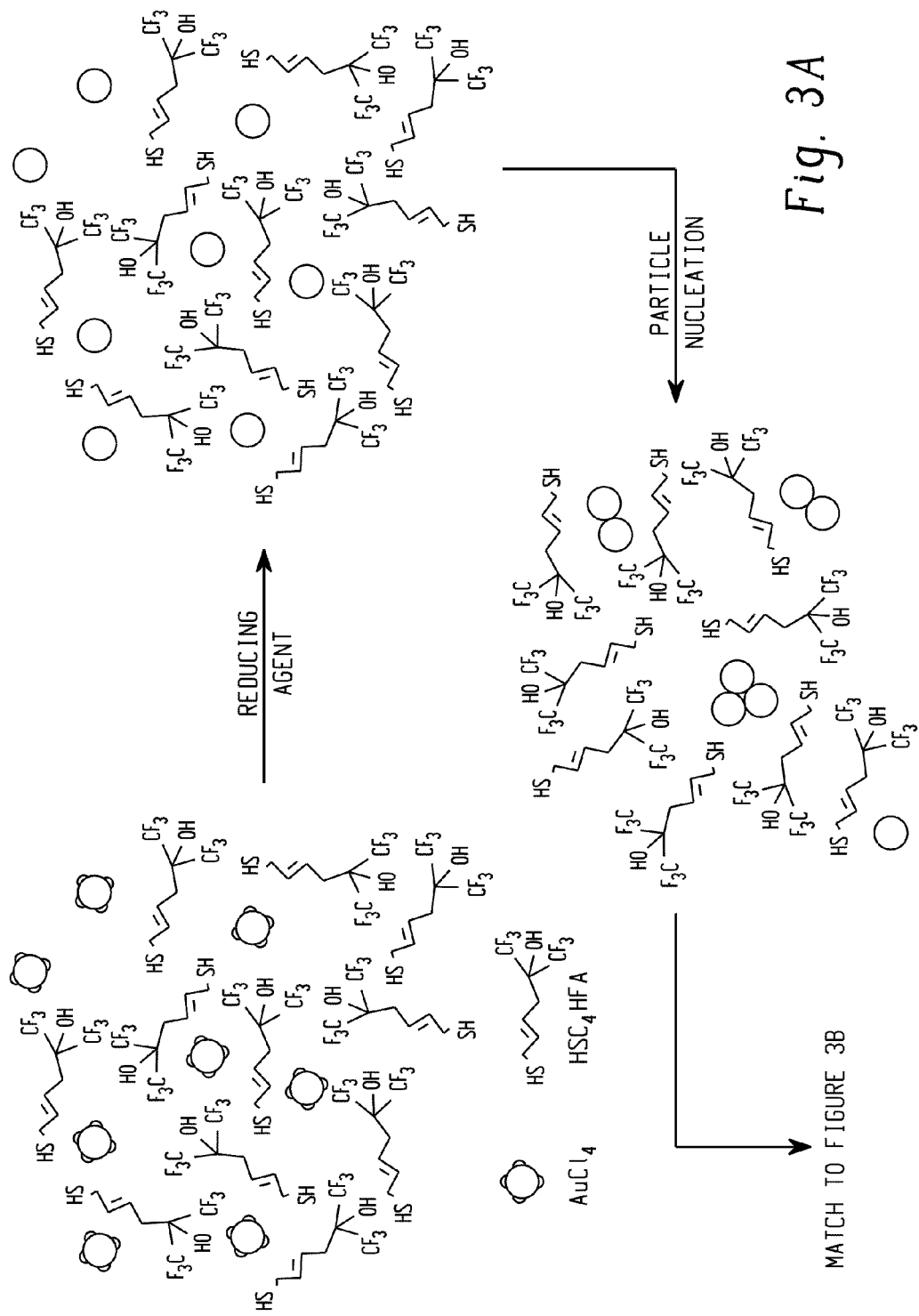
FIGS. 3A-3B illustrate a method preparing ligand encapsulated nanoparticles including the present compound by direct synthesis.
Figure 3B:
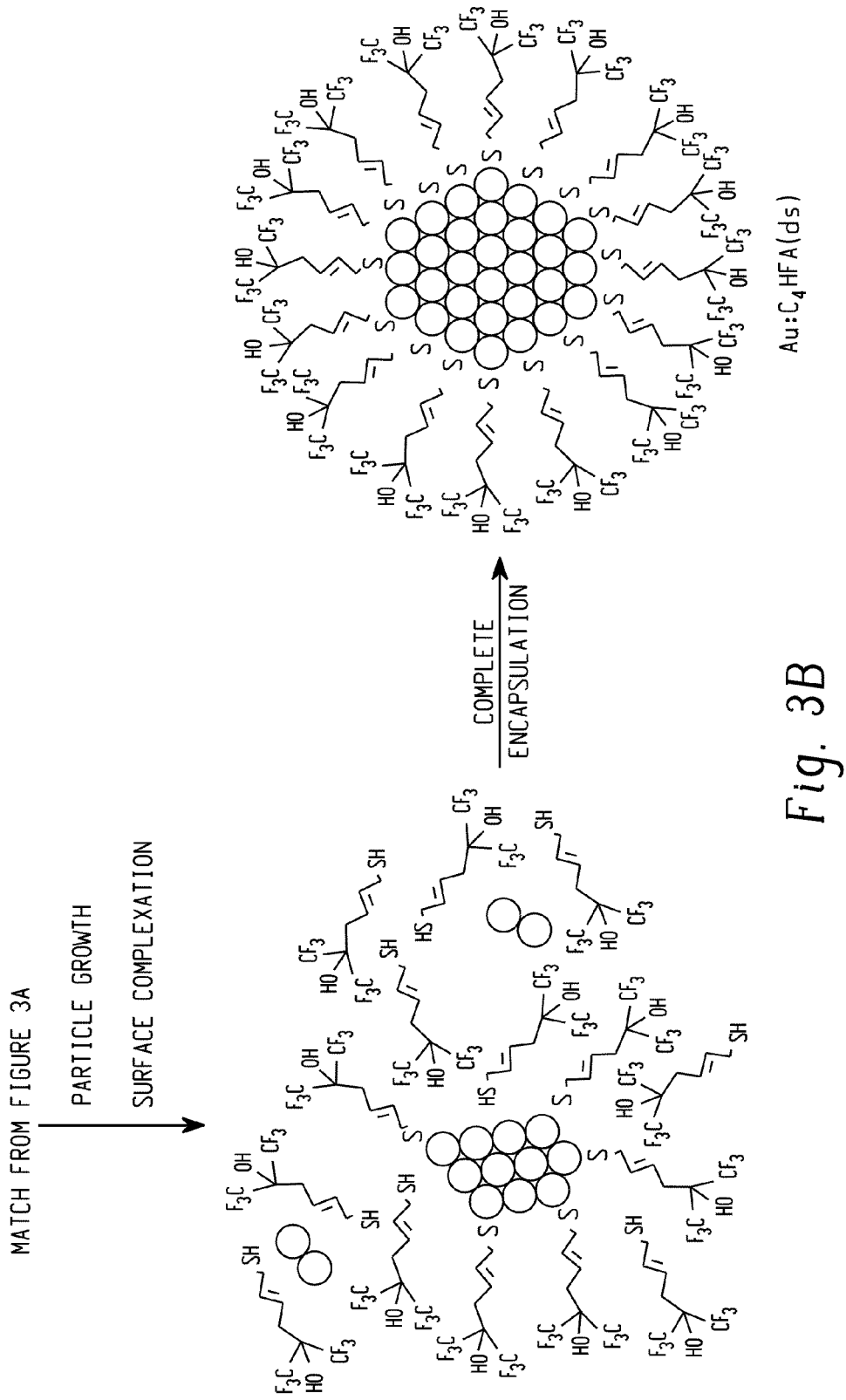
Figure 4A:
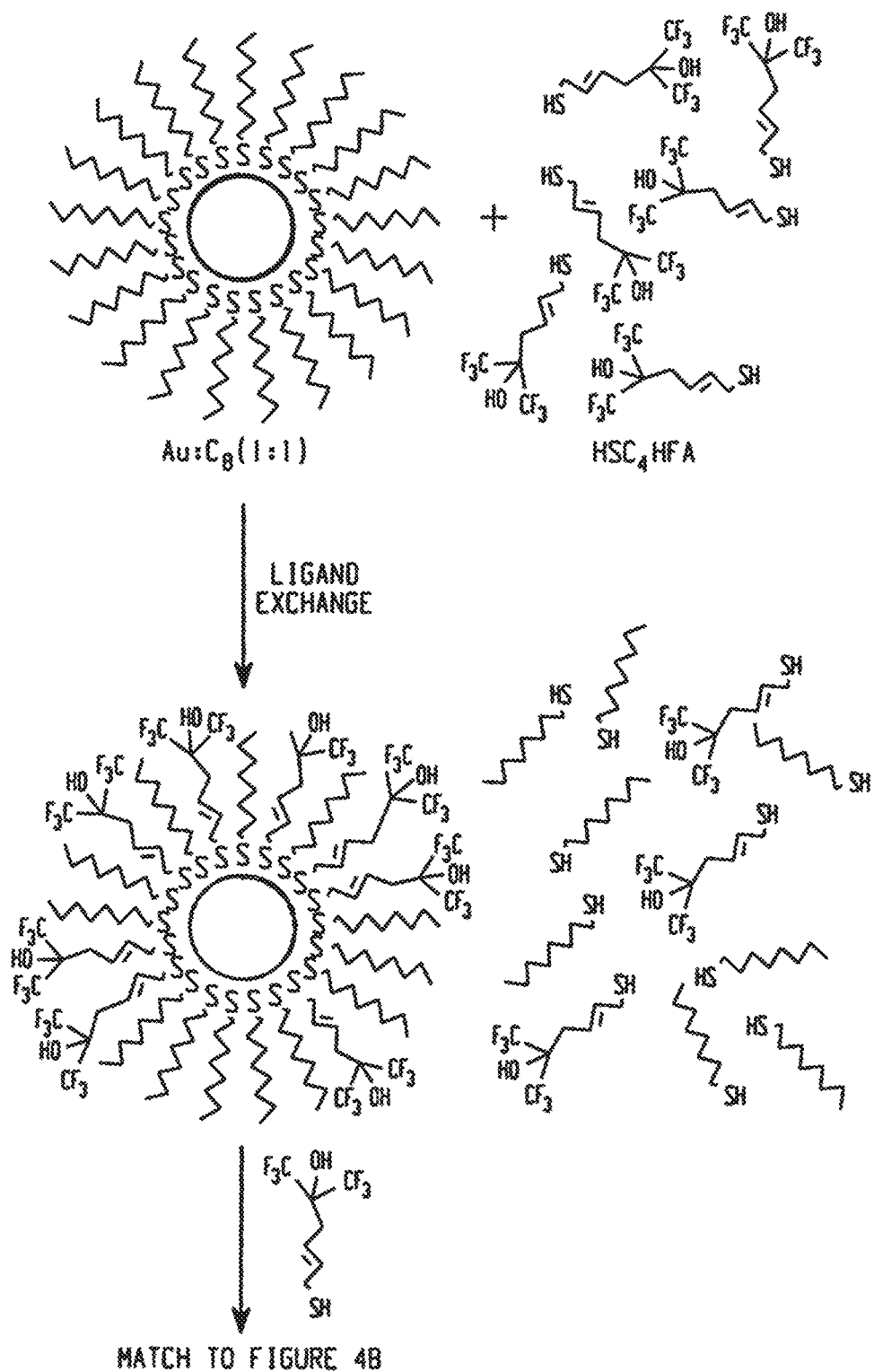
FIGS. 4A-4B illustrate a method of preparing ligand encapsulated nanoparticles including the present compound by exchange synthesis.
Figure 4B:
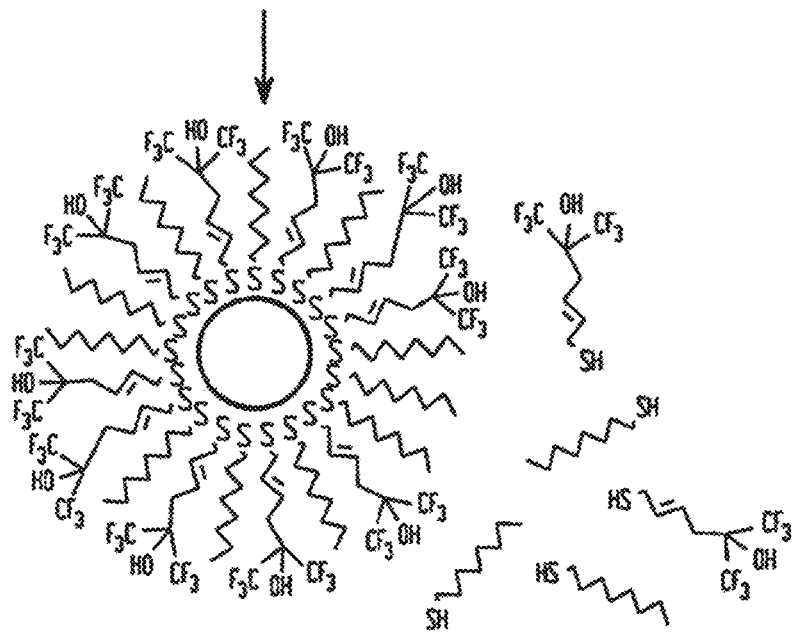
Figure 4B:
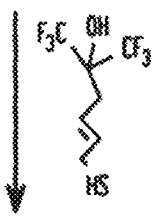
Figure 4B:
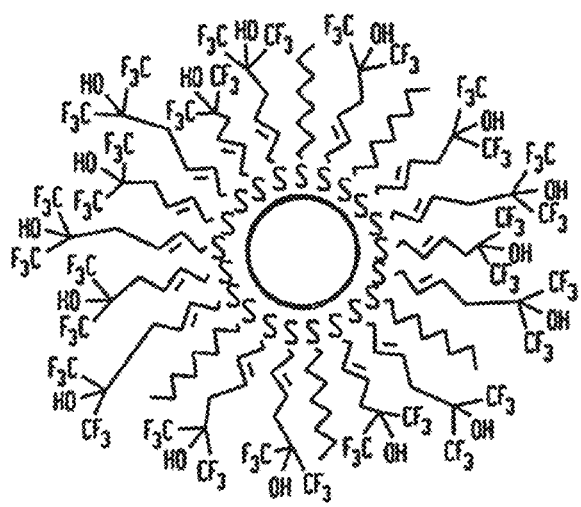

Two exemplary methods for preparation of hexafluorodimethylcarbinol terminated thiol ligand stabilized gold nanoclusters will now be described, as follows: (1) a direct synthesis; and, (2) an exchange synthesis. These methods are shown in FIGS. 2-4.

The direct synthesis method consists of dissolving a salt of the conductive metal (or salts of the conductive metal in embodiments utilizing alloys) of which the core is to be composed and an organic substance corresponding to the desired ligand in a common solvent (step S110). In one embodiment, a gold salt is utilized, which may include, but which is not limited to, $HAuCl_4$. The gold salt, the organic ligand and a reducing agent, such as $NaBH_4$ are dissolved in a common medium under conditions of rapid mixing (step S120) (this step may be performed as described in M. Brust et al., J. Chem. Soc., Chem. Comm. 1994, 801). In one embodiment, step S110 further employs a phase transfer reagent, such as, for example, tetraoctylammonium bromide. As depicted in FIG. 3 using, as the exemplary compound, 4-mercapto-2-butenyl-hexafluorodimethylcarbinol ($HSCH_2CH=CHCH_2C(CF_3)_2(OH)$ (similar to the compound of structure 4, above; a synthesis for production of which is described in Example 7), the gold ions of the salt are reduced to neutral atoms and subsequently nucleate to form multiatom cores (step S130, FIG. 2). These cores grow by adsorption of additional metal atoms. Competitively, the thiol ligand molecule is adsorbed onto the growing gold core surface (step S140), eventually encapsulating the gold core and terminating its growth. The relative stoichiometry of gold salt to organic thiol ligand determine the relative rates of gold core growth and thiol-ligand encapsulation, and thus the size of the core in the ligand-stabilized cluster. The thickness of the ligand shell is determined by the size of the thiol-ligand. Examples of this method of synthesis are given below as Example 7 and Example 8.

The exchange synthesis method consists of co-dissolving an alkanethiol stabilized cluster and a free hexafluorodimethylcarbinol terminated thiol for the ligand in a common solvent (step S150), during which an exchange reaction occurs whereby the free hexafluorodimethylcarbinol terminated thiol displaces the gold surface bound alkanethiol ligand and an equilibrium distribution of the two thiols in the free and gold surface bound state is approached. The free thiols are then separated, and a second exchange step may follow with the addition of more of the free hexafluorodimethylcarbinol terminated thiol (step S160). A new exchange equilibrium is approached where the displacement of the alkanethiol by the free hexafluorodimethylcarbinol terminated thiol ligand is more advanced. Additional exchange cycles can be conducted (step S170) so that the ligand shell composition of the cluster approaches 100% of the hexafluorodimethylcarbinol terminated thiol ligand. This exchange synthesis method is depicted in FIG. 4, and examples are given below as Example 9 and Example 10.

For ligand-stabilized gold nanoclusters with polar ligands that make the nanocluster soluble in polar organic solvents such as alcohols, esters, ketones and polar halocarbons, the exchange synthesis method can be utilized over the direct synthesis method. The nanocluster solubility makes separation of phase transfer agents (used in the direct synthesis approach) from the cluster product difficult. This separation can require chromatography, which limits the scale of the reaction to small amounts, reduces the yield of purified product, and adds to the cost. The exchange method, while generally requiring additional steps, takes advantage of a very facile and highly scalable preparation of a precursor cluster (alkanethiol stabilized gold clusters) by the direct synthesis method, and it avoids use of the phase transfer agent and its attendant purification difficulties. This exchange synthesis method also is a facile preparation route to nanoclusters with varying amounts of different ligands in the nanocluster shell, as described in Example 11 and Example 12.

Figure 5:
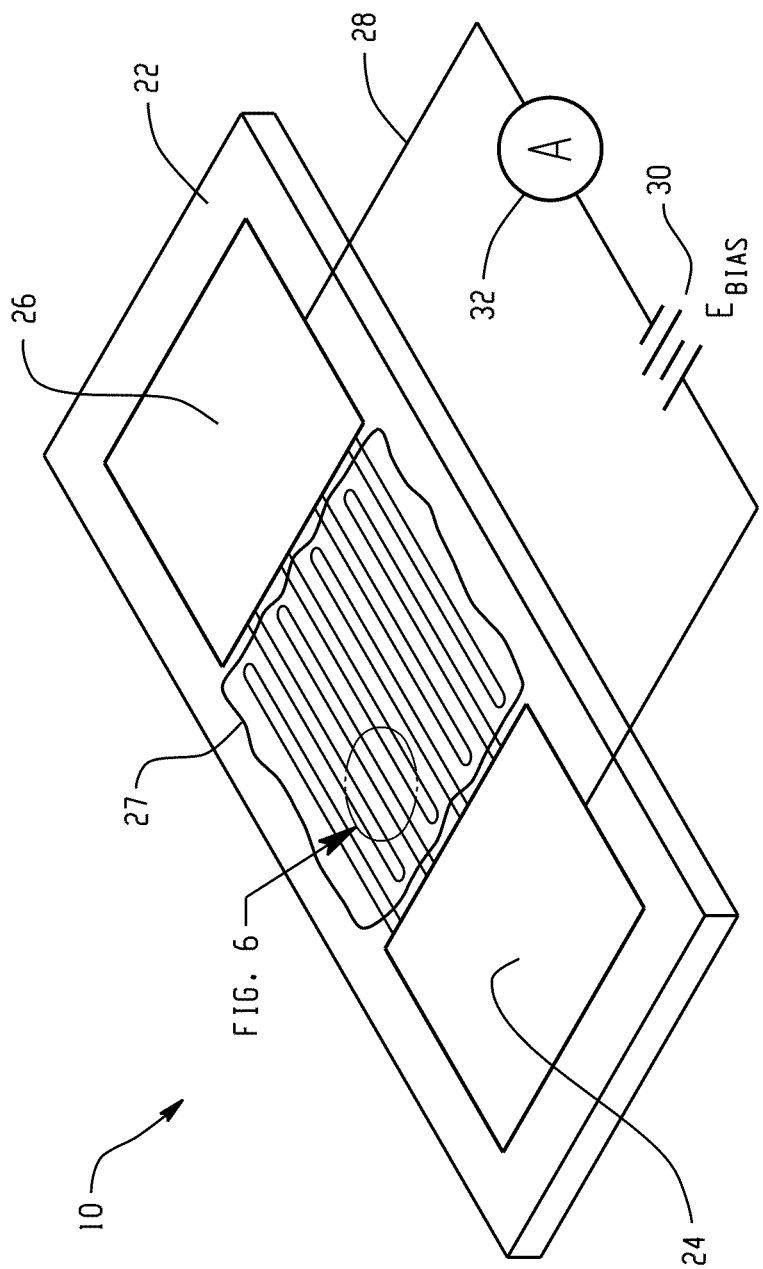
FIG. 5 is a perspective view of a sensor comprising a film of nanoparticles encapsulated by the exemplary hexafluorodimethylcarbinol terminated thiol compound.
Figure 6:
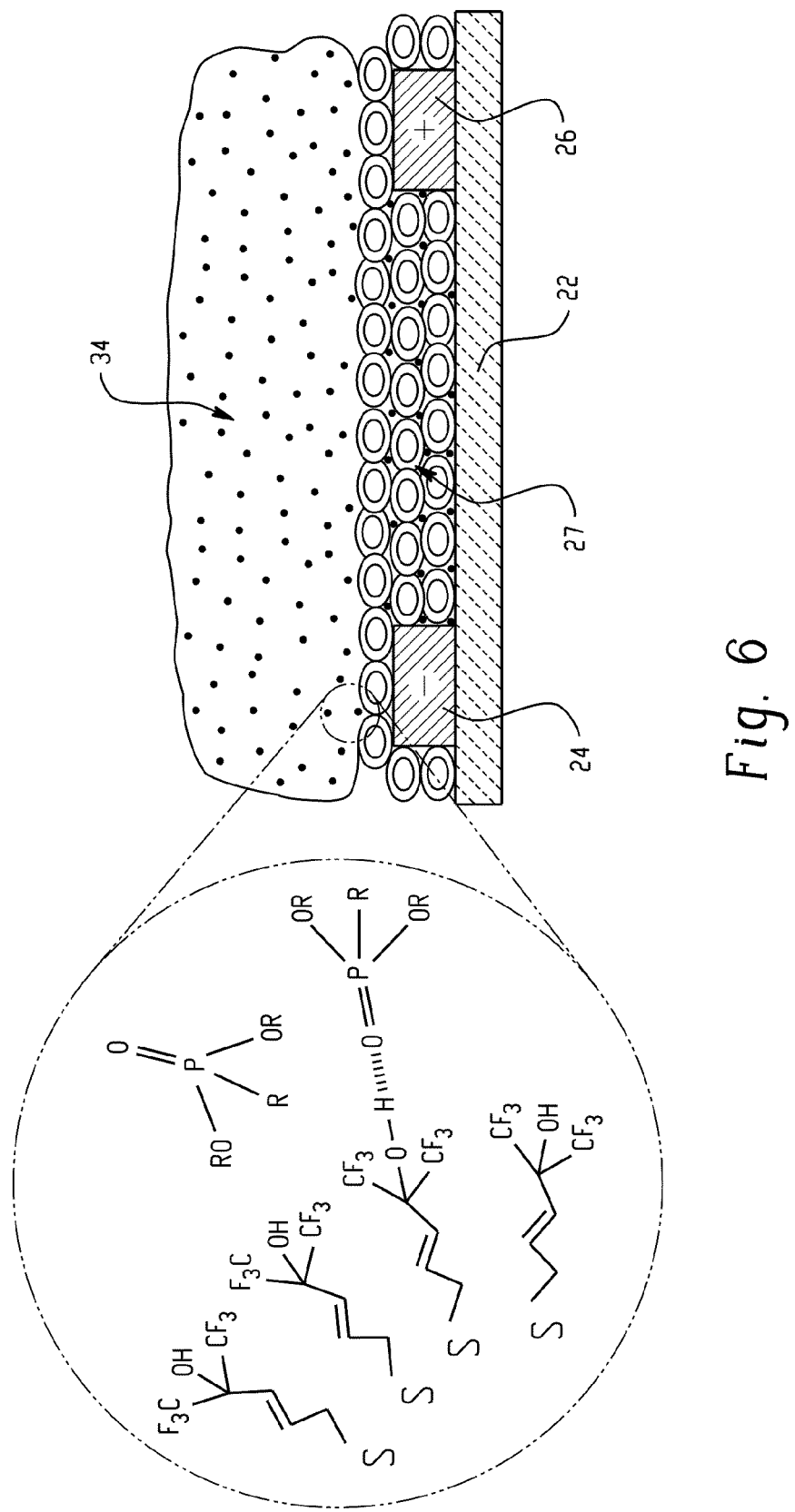
FIG. 6 shows a magnified representation of the hydrogen-bonded interaction between the hexafluorodimethylcarbinol moiety of a cluster ligand shell and a phosphonate ester vapor in a sensor configuration.
Figure 7:
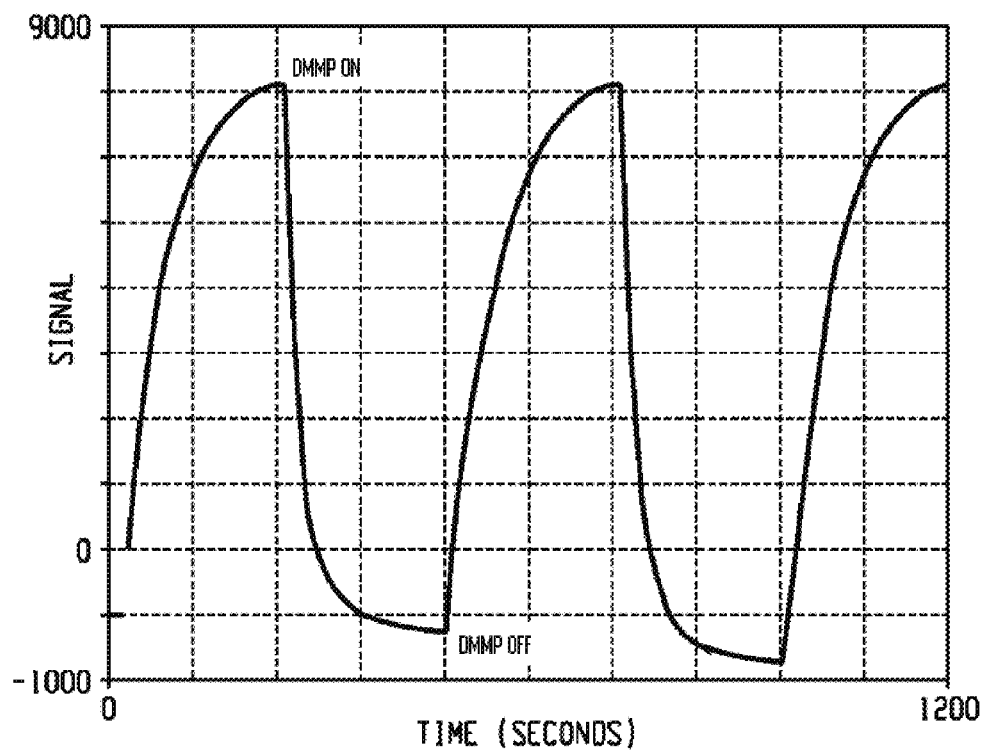
FIG. 7 is a graph showing a response of a sensor exposed to purge (DMMP off) and exposure (DMMP on) cycles of a phosphonate ester vapor delivered by a vapor generator, where the signal strength (arbitrary units) roughly corresponds to measured current; and, FIG. 8 is a graph showing the maximum magnitude response for a sensor vs. DMMP vapor concentration for a sensor based on a stabilized gold nanocluster comprising the hexafluorodimethylcarbinol terminated thiol compound in accordance with another exemplary embodiment of the present disclosure.
Figure 8:
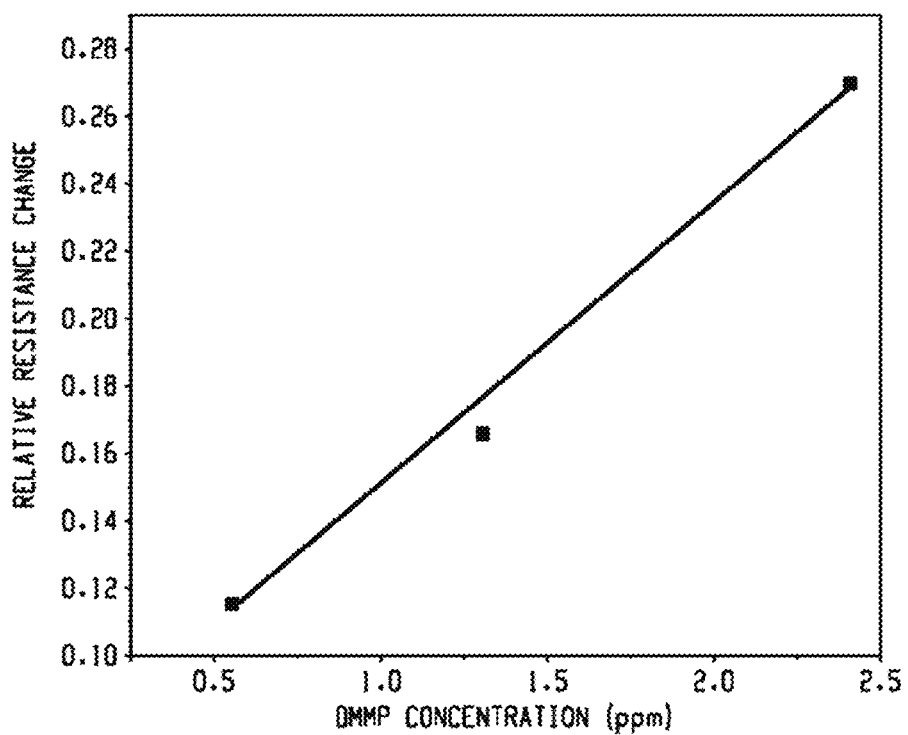

The encapsulated metal nanoparticles thus formed may be used as a vapor responsive electronic transducer in a chemical sensor. Embodiments of this disclosure can include a sensor having a metal surface comprised of gold, although other metals such as silver, platinum, palladium, or alloys thereof may be used. These ligand-stabilized gold nanocluster materials can become a component in a chemical sensor when these materials, comprising at least 0.1% by weight of the microencapsulated particles, are deposited as a continuous thin film onto a surface equipped with a pair of electrical contacts (step 180). The pair of electrical contacts can be used to detect electrical properties and changes in electrical properties of the coating that is positioned in the gap between the electrodes. When target molecules adsorb and desorb into and out of the nanocluster film, the accompanying electrical property change is transduced into an electronic signal by this sensing device. A very useful configuration for such electrical contacts on a surface is the interdigitated electrode, shown in FIG. 5, and described in further detail below, which may be fabricated on an insulating substrate as described in U.S. Pat. No. 6,221,673. This configuration of electrical contacts has a very large cross-sectional area to gap ratio, and the electrodes themselves are very closely spaced (ranging from 0.01 to 1000 micrometer and, in one embodiment, from 1 to 100 micrometer) and thin (ranging from 0.1 to 10 micrometer and, in one embodiment, from 0.50 to 5 micrometer). As also described in U.S. Pat. No. 6,221,673, there are several ways for depositing S180 the thin film of nanocluster materials onto the surface of an electrode device, which include spraying from solution as a fine mist, casting a film on the surface by evaporation of solvent from a deposited solution of clusters, and chemical self-assembly using coupling agents which bond individual clusters to the surface and to each other. Typical thicknesses of the deposited cluster film range from 0.005 to 10 micrometers. Once deposited, the film of clusters is characterized by a baseline electrical property in an inert environment. Such a property is any measurable response to application of an electrical field and includes a resistance, impedance, capacitance, etc. Typically, the resistance of the device ranges from 0.001 to 100 MΩ and in one embodiment in a range of 0.01 to 1 MΩ.

The sensor thus fabricated is then exposed to an environment (step S190) in which a concentration of a targeted chemical species resides. The chemical species may be present in the environment as a gas, vapor, aerosol, or liquid. When the sensor is exposed to the environment S190 containing phosphonate esters or other organophosphorus chemical warfare agents, the hexafluorodimethylcarbinol groups at the outer surface of the ligand stabilized nanoparticles interact with the phosphoryl substructure of the warfare agents in the environment (step S200). The interaction S200 can be detected by a change in the electrical property, such as the conductivity, of the sensor.

One chemical species which may be targeted by the sensor is the phosphonate ester class of compound, and the molecular interaction is one of a strong hydrogen bond donor (the hexafluorodimethylcarbinol moiety in the ligand shell of the cluster) interacting with a strong hydrogen bond acceptor (the phosphoryl functional group of a phosphonate ester compound) to form a hydrogen-bonded complex. FIG. 6 presents a depiction of this hydrogen-bonded interaction from a sensor perspective. In this depiction, there is a partitioning of the phosphonate ester between the vapor phase and that adsorbed by way of hydrogen bonding onto the ligand shell of the assembly of clusters forming the coating on the interdigital electrode sensing device. The adsorbed phosphonate ester perturbs the response of the ensemble of nanoclusters in the film to an electric field by way of changing the distances between neighboring metal nanoparticle cores and by altering the permittivity of the medium between these cores as well. The simplest electrical property to measure is the passage of current through the assembly of clusters in the gaps between the electrodes.

The relative resistance change of a sensor responding to phosphonate ester vapor exposure and purge cycles is shown in FIG. 7. A vapor exposure and purge cycle entails the alternate delivery of a stream of air with a known concentration of vapor for a fixed duration of time followed by a stream of pure air to purge the sensor housing for a fixed duration of time. The "on" part of the cycle refers to the vapor exposure, and the "off" part of the cycle refers to the pure air purge part of the cycle. The sensor device is coated with a film of 4-mercapto-2-butenyl-hexafluorodimethylcarbinol ligand-stabilized gold nanoclusters. The phosphonate ester is dimethylmethylphosphonate ($(CH_3O)_2CH_3PO$) (DMMP). DMMP is a frequently used physical simulant for phosphonate ester-based chemical warfare agents. The responses to this vapor are rapid and reversible. FIG. 8 shows the linear dependence of the same sensor response to varied concentrations of DMMP (in ppm). The slope of this line or simply a point within its range characterizes the sensitivity of the sensor. The detection limit extends to ppb and sub-ppb concentrations and is dependent on measurement electronics used.

Referring once more to FIG. 5, the exemplary sensor system 10 includes a substrate 22, which is formed of an electrically insulated material, such as quartz. A pair of interdigitated, electrically connected electrodes 24, 26, having comb-like configurations, is deposited on the substrate 22. The electrodes 24, 26 may be formed of gold fabricated on the quartz substrate 22. A thin film 27 composed of a multiplicity of ligand-stabilized nanoparticles formed using the exemplary compound is deposited on the interdigital electrodes 24, 26 and on the substrate surface between and in contact with the electrodes 24, 26. This thin film is an ensemble of closely packed nanoparticles having a core-shell structure sometimes referred to as a MIME (metal-insulator-metal ensemble) film. The cores are composed of an electrically conducting metal, in one embodiment, gold, and have a maximum diameter of less than 100 nm, and in one embodiment, less than 10 nm. The ligand shell is composed of an insulating material, but it has a thickness of a monomolecular layer. The thickness dimension of a monomolecular layer ranges from 0.3 to 2 nm, and at such dimensions electron transport may occur by way of tunneling currents through the insulator. The adsorption and desorption of analyte molecules to such thin insulating layers cause large changes in the tunneling current and the electric field permittivity between the metal cores. This MIME thin film is composed of a series of many metal-insulator-metal junctions and is deposited on the substrate 22 to connect the two electrodes 24, 26. A circuit 28, which includes electrodes 24, 26, including a voltage or power source 30 (e.g., a battery) and a current meter 32, or other electrical property measuring device, is used to measure an electrical property, such as conductivity. The sensor device 10 is exposed to an environment 34 (see FIG. 6) containing chemicals to be measured (e.g., gas, liquid, or solid). A reference device (not shown) may also be provided. The reference device is covered with a passivating layer (e.g., plastic, glass, paraffin wax, etc.), or in some other way is isolated from the environment, which possibly contains the chemical species of interest. The reference device provides a means to compensate for the normal change in resistance with temperature exhibited by the MIME in thin film applications.

The exemplary compounds disclosed herein are capable of being utilized in a variety of other applications. The adjacent fluorine and alcohol groups and the thiol functional group can confer unique properties on molecular substances. The compound may be present in a composition at from about 0.1 to about 100 mol %. For some applications, particularly the sensor coatings discussed above, the compound may be present at the upper end of the range. The compound can be present at lower levels for some applications, for example, from about 0.1 to about 5 mol % for other exemplary applications, including anti-corrosion coatings; surfactants, wetting and dispersing agents, defoamers, phase transfer agents, polymer blend formation promoters, and the like.

The hexafluorodimethylcarbinol group provides enhanced properties over the trifluoromethylcarbinol group in existing compounds. These properties include stronger hydrogen bonding, more proton acidity and greater hydrophobicity. This combination of enhanced properties makes these compounds improved surface active agents in aqueous systems. Furthermore, the hexafluorodimethylcarbinol portion of the compound improves sensitivity and selectivity of a point sensor for detection of the organophosphorus chemical warfare (e.g., nerve) agents, such as Sarin (GB), Soman (GD), and VX. When the present compound-coated sensor is exposed to an environment having phosphonate ester vapors (shown as step f in FIG. 1), the phosphoral ester group of the warfare agent can bond to two available hydrogen atoms of two adjacent trifluoromethylcarbinol groups.

The hexafluorodimethylcarbinol functionality of the compound can impart several advantages to the metal surfaces of which it is applied. First, the adjacent trifluoromethyl groups inductively promote hydroxyl acidity to both enhance hydrogen bonding and to sterically deter intramolecular bonding; and, (2) the fluorine presence makes the monolayer coating hydrophobic, which reduces the coating's sensitivity to water and, hence, discourages water-induced corrosion of the metal surface.

The thiol is capable of bonding interaction with metal atoms on a core surface of a nanocluster. Unlike existing compounds, the exemplary compound provides alkanethiol and alkenethiol compounds that include the hexafluorodimethylcarbinol group at one end of a chain and a thiol at the other. The hexafluorodimethylcarbinol terminated thiols are thus useful in applications for surface treatment of metals.

The exemplary embodiment discloses a novel synthetic route for forming a compound having both a hexafluorodimethylcarbinol and a thiol functional group. It further provides a novel compound having adjacent trifluoromethyl groups situated at a first end of a molecular carbon-containing chain and the thiol group situated at an opposite, second end of the chain.

A first advantage to various aspects of the present compound is that it may be produced at high yields as the synthesis is readily accomplished.

A second advantage to various aspects of the present compound is that having two trifluoromethyl groups in the hexafluorodimethylcarbinol functionality can enhance the unique properties associated with incorporation of a fluoroalcohol functional group. For example, the coating can be more hydrophobic in character; hence, it can improve sensor selectivity by mitigating the effects of moisture and humidity. In particular, the additional fluorine atoms of the adjacent trifluoromethyl groups can improve the hydrophobicity of the coatings for MIME sensors, as compared to a single trifluoromethyl group available in existing coatings. The disclosed compound can also provide less interference from water vapor in sensing applications.

The adjacent trifluoromethyl groups may provide another advantage of greater sensitivity to ester molecules in phosphonate ester vapors. In particular, an improved hydrogen bond interaction between the fluoroalcohol groups and a phosphoryl group present in organophosphorus chemical warfare agents is achieved, thereby improving detection when the compound is used in a sensor.

Having described the invention, the following examples are given to illustrate specific applications. These specific examples are not intended to limit a scope of the invention described in this application.

EXAMPLES

A. Production of Hexafluorodimethylcarbinol Terminated Alkane- and Alkenethiols

Example 1

Synthesis of 4-bromo-2-butenyl-hexafluorodimethylcarbinol ($BrCH_2CH=CHCH_2C(CF_3)_2(OH)$-mixed geometric isomers)

This compound was prepared by condensing 4-bromo-1-butene with hexafluoroacetone (analogous to step a of the exemplary synthesis shown above). The reaction was conducted in a 250 ml glass lined stainless steel Parr bomb fitted with a magnetic stirring bar. 4-Bromo-1-butene (4.15 g, 30.7 mmol) was first weighed into the glass liner of the Parr bomb. The bomb was assembled, cooled with liquid nitrogen, and evacuated. Gaseous hexafluoroacetone (12.8 g, 77.1 mmol) was then condensed into the bomb. The sealed bomb was heated to 135° C. with stirring for a reaction time of 72 hr. After cooling and pressure release, a dark liquid (11.04 g) crude product was obtained. Purification by distillation at reduced pressure yielded a water-white fraction (7.58 g, 82%) collected at 84-86° C./8 mm Hg, which was determined to be >99% pure by gas chromatography. IR (neat/NaCl): 3600 shoulder absorption ("sh") and 3500 (free and H-bonded O—H); 3060 weak absorption ("w") (olefinic C—H); 2960 w (aliphatic C—H); 1430 (olefinic C=C), 1200 strong absorption ("s") (C—F); 650 (C—Br). $^1$H NMR (CDCl$_3$): 2.72 and 2.80 (doublets, 2H, for cis-trans mixture =CH—CH$_2$—C(CF$_3$)$_2$(OH)); 3.00 (singlet-broad, 1H, O—H); 3.92 and 3.96 (doublets for cis-trans mixture Br—CH$_2$CH=); 5.77 (multiplet, 1H, =C—H); 5.92 (multiplet, 1H, =C—H). $^{13}$C NMR (CDCl$_3$): 25.0 and 27.5 (cis-trans mixture CH$_2$); 30.9 and 33.0 (cis-trans mixture CH$_2$); 75.1 (—C(CF$_3$)$_2$OH); 123.2 (quartet CF$_3$); 120.8 and 124.6 (cis-trans mixture C=); 131.9 and 134.0 (cis-trans mixture C=). $^{19}$F NMR (CDCl$_3$, Freon 113 reference) −77.02 and −77.17 (2 singlets, cis-trans mixture CF$_3$). Analysis calculated for C$_7$H$_7$BrF$_6$O: C, 27.93; H, 2.34. Found: C, 27.84; H, 2.40.

Example 2

Synthesis of 4-mercapto-2-butenyl-hexafluorodimethylcarbinol (HSCH$_2$CHCHCH$_2$C(CF$_3$)$_2$(OH)-mixed geometric isomers)

This compound was prepared by reacting 4-bromo-2-butenyl-hexafluorodimethylcarbinol (product of Example 1) with thiourea to form the intermediate isothiouronium salt (similar to step c of the exemplary synthesis shown above) which was subsequently hydrolyzed by a base (NaOH) to the thiol (analogous to step d of the exemplary synthesis shown above). This reaction was conducted in a two-neck 25 ml round bottom flask fitted with a magnetic stirring bar, reflux condenser and thermometer under a nitrogen atmosphere. 4-Bromo-2-butenyl-hexafluorodimethylcarbinol (2.00 g, 6.64 mmol) was weighed into the reaction vessel followed by ethanol (5.0 ml) and thiourea (0.52 g, 6.73 mmol). This solution was refluxed at 80° C. for 3 hr. Sodium hydroxide (0.37 g, 9.2 mmol) dissolved in water (5.0 ml) was added, and the reaction mixture was refluxed at 85° C. for 3 hr. The reaction was worked up by dropwise addition of the reaction mixture to 25 ml distilled water. This mixture was neutralized by dropwise addition of 1.0 M HCl until just acidic (pH paper test) then extracted 3 times with 10 ml methylene chloride. The combined methylene chloride extracts were back extracted 2 times with 10 ml portions of distilled water and dried over anhydrous sodium sulfate. After filtering and rotary evaporation (50° C./20 mm Hg), 1.52 g of a yellow oil crude product were obtained. This was purified by vacuum distillation to yield a fraction (1.04 g, 62%) collected at 75° C./5 mm Hg, which was determined to be >99% pure by gas chromatography. IR (neat/NaCl): 3600 (sh) and 3500 (free and H-bonded O—H); 3060 w (olefinic C—H); 2960 w (aliphatic C—H); 2560 w (thiol S—H); 1430 (olefinic C=C), 1200 s (C—F). $^1$H NMR (CDCl$_3$): 1.47 and 1.61 (triplets, 1H, for cis-trans mixture S—H); 2.68 and 2.75 (doublets, 2H, for cis-trans mixture =CH—CH$_2$—C(CF$_3$)$_2$(OH)); 3.10 (singlet-broad, 1H, O—H); 3.17 and 3.19 (triplets for cis-trans mixture HS—CH$_2$CH=); 5.55 (multiplet, 1H, =C—H); 5.82 (multiplet, 1H, =C—H). $^{13}$C NMR (CDCl$_3$): 20.3 and 26.2 (cis-trans mixture CH$_2$); 28.0 and 33.1 (cis-trans mixture CH$_2$); 75.1 (—C(CF$_3$)$_2$OH); 123.0 (quartet, CF$_3$); 120.0 and 121.0 (cis-trans mixture C=); 135.3 and 137.7 (cis-trans mixture C=). $^{19}$F NMR (CDCl$_3$, Freon 113 reference) −76.84 and −77.05 (2 singlets, cis-trans mixture CF$_3$). Analysis calculated for C$_7$H$_8$F$_6$OS: C, 33.08; H, 3.17. Found: C, 32.98; H, 3.27.

Example 3

Synthesis of 5-bromo-3-pentenyl-hexafluorodimethylcarbinol (BrCH$_2$CH$_2$CH=CHCH$_2$C(CF$_3$)$_2$(OH)-mixed geometric isomers) (structure 2)

This compound was prepared by condensing 5-bromo-1-pentene (structure 1) with hexafluoroacetone (step a of the exemplary synthesis shown above). The reaction was conducted in a 250 ml glass lined stainless steel bomb fitted with a magnetic stirring bar. 5-Bromo-1-pentene (4.36 g, 29.3 mmol) was weighed into the glass liner of the Parr bomb. The bomb was assembled, cooled with liquid nitrogen and evacuated. Gaseous hexafluoroacetone (13.6 g, 81.9 mmol) was then condensed into the bomb. The sealed bomb was heated to 140° C. with stirring for a reaction time of 72 hr. After cooling and pressure release, a dark liquid (9.20 g) crude product was obtained. Purification by distillation at reduced pressure yielded a water-white fraction (8.50 g, 92%) collected at 65° C./1 mm Hg, which was determined to be >99% pure by gas chromatography. IR (neat/NaCl): 3600 (sh) and 3500 (free and H-bonded O—H); 3060 w (olefinic C—H); 2960 w (aliphatic C—H); 1430 (olefinic C=C), 1200 s (C—F); 650 (C—Br). $^1$H NMR (CDCl$_3$): 2.65 (broad multiplet, 4H, =CH—CH$_2$); 3.10 (singlet-broad, 1H, O—H); 3.43 (triplet, 2H, Br—CH$_2$—); 5.55 (multiplet, 1H, =C—H); 5.7 (multiplet, 1H, =C—H). $^{13}$C NMR (CDCl$_3$): 28.2 and 30.5 (cis-trans mixture CH$_2$); 32.4 and 33.5 (cis-trans mixture CH$_2$); 35.2 CH$_2$; 74.8 (—C(CF$_3$)$_2$OH); 123.1 (quartet CF$_3$); 121.3 and 123.2 (cis-trans mixture C=); 134.5 and 136.8 (cis-trans mixture C=). $^{19}$F NMR (CDCl$_3$, Freon 113 reference) −77.13 and −77.33 (2 singlets, cis-trans mixture CF$_3$). Analysis calculated for C$_8$H$_9$BrF$_6$O: C, 30.50; H, 2.88. Found: C, 30.44; H, 2.95.

Example 4

Synthesis of 5-mercapto-3-pentenyl-hexafluorodimethylcarbinol (HSCH$_2$CH$_2$CH=CHCH$_2$C(CF$_3$)$_2$(OH)-mixed geometric isomers) (structure 4)

This compound was prepared by reacting 5-bromo-1-pentenyl-hexafluorodimethylcarbinol (structure 2, product of Example 3) with thiourea to form the intermediate isothiouronium salt, which was subsequently hydrolyzed by a base to the thiol as for Example 2. This reaction was conducted in a two-neck 25 ml round bottom flask fitted with a magnetic stirring bar, reflux condenser and thermometer under a nitrogen atmosphere. 5-Bromo-2-pentenyl-hexafluorodimethylcarbinol (2.50 g, 7.93 mmol) were weighed into the reaction vessel followed by ethanol (5.0 ml) and thiourea (0.612 g, 8.04 mmol). This solution was refluxed at 84° C. for 2.5 hr. Sodium hydroxide (0.44 g, 11.0 mmol) dissolved in water (5.0 ml) was added, and the reaction mixture was refluxed at 87° C. for 2.5 hr. The reaction was worked up by dropwise addition of the reaction mixture to 25 ml distilled water. This mixture was neutralized by dropwise addition of 1.0 M HCl until just acidic (pH paper test) then extracted 3 times with 20 ml methylene chloride. The combined methylene chloride extracts were back extracted 2 times with 10 ml portions distilled water and dried over anhydrous sodium sulfate. After filtering and rotary evaporation (50° C./20 mm Hg), 1.84 g a yellow oil crude product were obtained. This was purified by vacuum distillation to yield a fraction (1.32 g, 65%) collected at 65° C./1 mm Hg, which was determined to be >99% pure by gas chromatography. IR (neat/NaCl): 3600 (sh) and 3470 (free and H-bonded O—H); 3050 w (olefinic C—H); 2940 w (aliphatic C—H); 2550 w (thiol S—H); 1430 (olefinic C═C), 1200 s (C—F). $^1$H NMR (CDCl$_3$): 1.30 and 1.42 (triplets, 1H, for cis-trans mixture S—H); 2.38 (multiplet, 2H, CH$_2$SH); 2.61 (multiplet, 2H, for cis-trans mixture ═CH—$\overline{CH_2}$); 2.70 and 2.75 (doublets, 2H, for cis-trans mixture ═CH—C$\overline{H_2}$—C(CF$_3$)$_2$(OH)); 3.33 (singlet-broad, 1H, O—H); 5.49 (multiplet, 1H, ═C—H); 5.65 (multiplet, 1H, ═C—H). $^{13}$C NMR (CDCl$_3$): 23.9 and 27.3 (cis-trans mixture CH$_2$); 30.1 and 33.4 (cis-trans mixture CH$_2$); 36.1 CH$_2$; 123.1 (quartet CF$_3$); 121.2 and 123.0 (cis-trans mixture C═); 136.2 and 138.0 (cis-trans mixture C═). $^{19}$F NMR (CDCl$_3$, Freon 113 reference) −77.11 and −77.33 (2 singlets, cis-trans mixture CF$_3$). Analysis calculated for C$_8$H$_{10}$F$_6$OS: C, 35.82; H, 3.76. Found: C, 35.79; H, 3.79.

Example 5

Synthesis of 5-bromopentyl-hexafluorodimethyl-carbinol (BrCH$_2$CH$_2$CH$_2$CH$_2$CH$_2$C(CF$_3$)$_2$(OH)) (structure 3)

This compound was prepared by hydrogenating (step b of the exemplary synthesis shown above) 5-bromo-3-pentenyl-hexafluorodimethylcarbinol (structure 2, product of Example 3) over a 10% palladium/carbon catalyst. The reaction was conducted in a 250 ml glass lined stainless steel bomb fitted with a magnetic stirring bar. The 10% palladium/carbon catalyst (0.25 g), ethanol (25 ml) and 4-bromo-2-butenyl-hexafluorodimethylcarbinol (2.00 g, 6.35 mmol) were weighed into the glass liner of the Parr bomb. The bomb was assembled, cooled with liquid nitrogen, evacuated, charged with hydrogen, pumped out and recharged with hydrogen at an initial pressure of 1050 psi. This reaction was stirred at 22° C. for 72 hr during which the pressure dropped to 1010 psi. After pressure release, the bomb was opened and the liquid mixture filtered through Celite to remove the particulate carbon and yield a clear yellow solution which was reduced to 3.20 g of a yellow oil after evaporation of the ethanol. Vacuum distillation of the oil yielded two fractions, one of 1.35 g collected at 50-55° C./5 mm and the second of 0.60 g collected at 80-90° C./5 mm. The second fraction (28% yield) was 95% pure by gas chromatography and analyzed as the product. IR (neat/NaCl): 3600 (sh) and 3500 (free and H-bonded O—H); 2950 m and 2900 w (aliphatic C—H); 1200 s (C—F). $^1$H NMR (CDCl$_3$): 1.48 (broad multiplet, 4H, —CH$_2$—); 1.88 (multiplet, 4H, —CH$_2$—); 2.84 (broad singlet, 1H, O—H); 3.49 (triplet, 2H, $\overline{BrCH_2}$—). $^{13}$C NMR (CDCl$_3$): 20.9, 28.5, 30.7, 32.4 and 34.0 (CH$_2$); 76.5 (—C(CF$_3$)$_2$OH); 123.1 (quartet CF$_3$). $^{19}$F NMR (CDCl$_3$, Freon 113 reference) −77.10 (singlet, CF$_3$). Analysis calculated for C$_8$H$_{11}$BrF$_6$O: C, 30.30; H, 3.50. Found: C, 30.19; H, 3.61.

Example 6

Synthesis of 5-mercaptopentyl-hexafluorodimethyl-carbinol (HSCH$_2$CH$_2$CH$_2$CH$_2$CH$_2$C(CF$_3$)$_2$(OH)- mixed geometric isomers) (structure 5)

This compound was prepared by reacting 5-bromopentyl-hexafluorodimethylcarbinol (structure 3, product of Example 5) with thiourea to form the intermediate isothiouronium salt, which was subsequently hydrolyzed by a base to the thiol as for Example 2. This reaction was conducted in a two-neck 25 ml round bottom flask fitted with a magnetic stirring bar, reflux condenser and thermometer under a nitrogen atmosphere. 5-Bromopentyl-hexafluorodimethylcarbinol (0.60 g, 1.89 mmol) were weighed into the reaction vessel followed by ethanol (5.0 ml) and thiourea (0.146 g, 1.92 mmol). This solution was refluxed at 81° C. for 3 hr. Sodium hydroxide (0.10 g, 2.62 mmol) dissolved in water (3.0 ml) was added, and the reaction mixture was refluxed at 84° C. for 3 hr. The reaction was worked up by dropwise addition of the reaction mixture to 10 ml distilled water. This mixture was neutralized by dropwise addition of 1.0 M HCl until just acidic (pH paper test) then extracted 3 times with 10 ml methylene chloride. The combined methylene chloride extracts were back extracted 2 times with 5 ml portions distilled water and dried over anhydrous sodium sulfate. After filtering and rotary evaporation (50° C./20 mm Hg), 0.43 g a yellow oil crude product were obtained. This was purified by vacuum distillation to yield a fraction (0.26 g, 51%) collected at (80-90° C./1 mm Hg) determined to be >90% pure by gas chromatography. IR (neat/NaCl): 3600 (sh) and 3470 (free and H-bonded O—H); 2950 w (aliphatic C—H); 2560 w (thiol S—H); 1200 s (C—F). $^1$H NMR (CDCl$_3$): 1.40 (triplet, 1H, S—H); 1.45 (broad multiplet, 4H, —CH$_2$—); 1.68 (multiplet, 2H, CH$_2$); 1.88 (multiplet, 2H, CH$_2$); $\overline{2}$.34 (multiplet, 2H, CH$_2$SH); $\overline{3}$.23 (singlet-broad, 1H, O—H); $^{13}$C NMR (CDCl$_3$): 20.6, 25.6, 28.1, 30.4 and 33.2 (CH$_2$); 77.8 (—C(CF$_3$)$_2$OH); 123.2 (quartet CF$_3$). $^{19}$F NMR (CDCl$_3$, Freon 113 reference) −77.05 (singlet, CF$_3$). Analysis calculated for C$_8$H$_{12}$F$_6$OS: C, 35.56; H, 4.48. Found: C, 35.48; H, 4.55.

B Preparation of Gold Nanoclusters Using Fluoroalcohol Ligands of the Exemplary Compounds Example 7

Direct synthesis method for gold nanocluster stabilized by 4-mercapto-2-butenyl-hexafluorodimethyl-carbinol (HSCH$_2$CH═CHCH$_2$C(CF$_3$)$_2$(OH))

Solutions of: 1.52 g tetraoctylammonium bromide ((C$_8$H$_{17}$)$_4$NBr) in 56 ml toluene; 0.2865 (0.727 mmol) hydrogen tetrachloroaurate (III) trihydrate (HAuCl$_4$.3H$_2$O) in 21 ml distilled water (analogous to step S110 above); 0.1847 g (0.727 mmol) 4-mercapto-2-butenyl-hexafluorodimethyl-carbinol (HSCH$_2$CH═CHCH$_2$C(CF$_3$)$_2$(OH)) in 2 ml toluene; and 0.2800 g (7.4 mmol) sodium borohydride (NaBH$_4$) (analogous to step S120 above) in 17.5 ml distilled water are prepared. With rapid stirring the HAuCl$_4$/water solution is slowly added to the (C$_8$H$_{17}$)$_4$NBr/toluene solution. After 2 minutes, the HSCH$_2$CH═CHCH$_2$C(CF$_3$)$_2$(OH)/toluene solution is added followed by the slow addition of the NaBH$_4$/water solution with very rapid stirring. The vigorous stirring is continued for 3 hr. The toluene phase is then separated and concentrated (55° C./25 mm rotary evaporation) to a 5 ml volume. This concentrated reaction mixture is added dropwise to 100 ml stirred diethyl ether, and the precipitated product collected by centrifugation as a thick oily crude product. After washing three times with 10 ml portions of diethyl ether, the crude product is purified by column chromatography. The product is dissolved in 2 ml CHCl$_3$, loaded onto a chromatographic column of silica packed in CHCl$_3$ and eluted with ethyl acetate to yield 0.31 g product. Subsequent elution with CH$_3$OH yields 0.15 g of cluster contaminated with (C$_8$H$_{17}$)$_4$NBr. The IR spectrum of the purified product is identical to that of the HSCH$_2$CH═CHCH$_2$C(CF$_3$)$_2$(OH) free thiol with the exception of the disappearance of the 2560 cm$^{-1}$ S—H stretch.

Example 8

Direct synthesis method for gold nanocluster stabilized by 5-mercapto-3-pentenyl-hexafluorodimethylcarbinol ($HSCH_2CH_2CH=CHCH_2C(CF_3)_2(OH)$) (structure 4)

Solutions of: 1.52 g tetraoctylammonium bromide (($C_8H_{17})_4NBr$) in 56 ml toluene; 0.2851 (0.724 mmol) hydrogen tetrachloroaurate (III) trihydrate ($HAuCl_4.3H_2O$) in 21 ml distilled water (analysis similar to step S110 above); 0.1917 g (0.715 mmol) 5-mercapto-3-pentenyl-hexafluorodimethylcarbinol ($HSCH_2CH_2CH=CHCH_2C(CF_3)_2(OH)$) in 2 ml toluene; and 0.2785 g (7.37 mmol) sodium borohydride ($NaBH_4$) (analogous to step S120 above) in 17.5 ml distilled water are prepared. With rapid stirring the $HAuCl_4$/water solution is slowly added to the ($C_8H_{17})_4NBr$/toluene solution. After 2 minutes, the $HSCH_2CH_2CH=CHCH_2C(CF_3)_2(OH)$/toluene solution is added followed by the slow addition of the $NaBH_4$/water solution with very rapid stirring. The vigorous stirring is continued for 3 hr. The toluene phase is then separated and concentrated (50° C./50 mm rotary evaporation) to a 5 ml volume. This concentrated reaction mixture is added dropwise to 100 ml stirred diethyl ether, and the precipitated product collected by centrifugation as a thick oily crude product. After washing three times with 10 ml portions of diethyl ether, the crude product is purified by column chromatography. The product is dissolved in 2 ml $CHCl_3$, loaded onto a chromatographic column of silica packed in $CHCl_3$ and eluted with ethyl acetate to yield 0.20 g product. Subsequent elution with $CH_3OH$ yields 0.23 g of cluster contaminated with ($C_8H_{17})_4NBr$. The IR spectrum of the purified product is identical to that of the $HSCH_2CH_2CH=CHCH_2C(CF_3)_2(OH)$ free thiol with the exception of the disappearance of the 2560 $cm^{-1}$ S—H stretch.

Example 9

Ligand exchange method for synthesis of gold nanocluster stabilized by 4-mercapto-2-butenyl-hexafluorodimethylcarbinol ($HSCH_2CH=CHCH_2C(CF_3)_2(OH)$)

Three successive exchange steps were conducted. To a 50 ml pear shaped flask fitted with a stirring bar and tight fitting cap were added 1.11 g Au:C8(1:1) (a gold nanocluster formed from $HAuCl_4$ and octanethiol (analogous to step S150 above), see U.S. Pat. No. 6,221,673), 2.0 ml $CHCl_3$ and 0.7767 g $HSCH_2CH=CHCH_2C(CF_3)_2(OH)$. The reaction mixture was stirred for 24 hours then concentrated to dryness by rotary evaporation followed by vacuum drying (1 mm/23° C.) and a 15 ml pentane rinse/decant to remove free thiol. For the second step, 0.7716 g $HSCH_2CH=CHCH_2C(CF_3)_2(OH)$ and 20 ml $CH_3OH$ were added to the exchange product in the reaction flask (analogous to step S150 above) The solution was again stirred for 24 hr then concentrated to dryness by rotary evaporation followed by vacuum drying (1 mm/23° C.) and a 15 ml pentane rinse/decant to remove free thiol. For the third step, 0.7777 g $HSCH_2CH=CHCH_2C(CF_3)_2(OH)$ and 20 ml $CH_3OH$ were added to the reaction flask (analogous to step S170 above). This solution was again stirred for 24 hr followed by concentration to dryness by rotary evaporation, vacuum drying (1 mm/23° C.) and a 15 ml pentane rinse/decant to remove free thiol. The product was then extracted 12 hr with pentane and vacuum dried to yield 0.8122 g. The IR spectrum was identical to that of the $HSCH_2CH=CHCH_2C(CF_3)_2(OH)$ free thiol with the exception of the disappearance of the 2560 $cm^{-1}$ S—H stretch.

Example 10

Ligand exchange method for synthesis of gold nanocluster stabilized by 5-mercapto-3-pentenyl-hexafluorodimethylcarbinol ($HSCH_2CH_2CHCHCH_2C(CF_3)_2(OH)$) (structure 4)

Three successive exchange steps were conducted. To a 50 ml pear shaped flask fitted with a stirring bar and tight fitting cap were added 0.1500 g Au:C8(1:1) (as described above), 2.0 ml $CHCl_3$ and 0.1706 g $HSCH_2CH_2CH=CHCH_2C(CF_3)_2(OH)$. The reaction mixture was stirred for 24 hours then concentrated to dryness by rotary evaporation followed by vacuum drying (1 mm/23° C.) and a 2 ml pentane rinse/decant to remove free thiol. For the second step, 0.1026 g $HSCH_2CH=CHCH_2C(CF_3)_2(OH)$ and 1.5 ml 2-propanol were added to the exchange product in the reaction flask (analogous to step S150 above). The solution was again stirred for 24 hr then concentrated to dryness by rotary evaporation followed by vacuum drying (1 mm/23° C.) and a 2 ml pentane rinse/decant to remove free thiol. For the third step, 0.0998 g $HSCH_2CH=CHCH_2C(CF_3)_2(OH)$ and 1.5 ml $CH_3OH$ were added to the reaction flask (analogous to step S170 above). This solution was again stirred for 24 hr followed by concentration to dryness by rotary evaporation, vacuum drying (1 mm/23° C.) and three cycles of 2 ml pentane rinse/decant to remove free thiol. The product was then extracted 12 hr with pentane and vacuum dried to yield 0.2513 g. The IR spectrum was identical to that of the $HSCH_2CH=CHCH_2C(CF_3)_2(OH)$ free thiol with the exception of the disappearance of the 2560 $cm^{-1}$ S—H stretch.

Example 11

Ligand exchange method for synthesis of gold nanocluster stabilized by a mixture 4-mercapto-2-butenyl-hexafluorodimethylcarbinol ($HSCH_2CH=CHCH_2C(CF_3)_2(OH)$) and hexanethiol ($HS(CH_2)_5CH_3$)

One exchange step was conducted. To a 10 ml pear-shaped flask fitted with a tight fitting cap were added 0.1012 g Au:C6 (1:1) (a gold nanocluster formed from $HAuCl_4$ and hexanethiol, see U.S. Pat. No. 6,221,673), 2.0 ml $CHCl_3$ and 0.0193 g $HSCH_2CH=CHCH_2C(CF_3)_2(OH)$. The reaction mixture was stirred for 24 hours then concentrated to dryness by rotary evaporation followed by vacuum drying (1 mm/23° C.). The product was rinsed two times with 2 ml quantities of pentane in which it has a slight solubility and vacuum dried (1 mm/23° C.) to yield 0.0870 g. The quantities of product in the first and second pentane washes were 0.0059 g and 0.0023 g respectively. IR spectra displayed bands characteristic of both the $HSCH_2CH=CHCH_2C(CF_3)_2(OH)$ and the $HS(CH_2)_5CH_3$ ligands, and, from the C—F stretching (1200 $cm^{-1}$) and C—H stretching of the $CH_3$ group, a relative ligand composition of 2:3 $HSCH_2CH=CHCH_2C(CF_3)_2(OH)$: $HS(CH_2)_5CH_3$ was determined for the shell.

Example 12

Ligand exchange method for synthesis of gold nanocluster stabilized by a mixture 5-mercapto-3-pentenyl-hexafluorodimethylcarbinol ($HSCH_2CH_2CH=CHCH_2C(CF_3)_2(OH)$) (structure 4) and hexanethiol ($HS(CH_2)_5CH_3$)

One exchange step was conducted. To a 10 ml pear-shaped flask fitted with a tight fitting cap were added 0.1022 g Au:C6

(1:1) (as above), 2.0 ml CHCl$_3$ and 0.0203 g HSCH$_2$CH=CHCH$_2$C(CF$_3$)$_2$(OH). The reaction mixture was stirred for 24 hours then concentrated to dryness by rotary evaporation followed by vacuum drying (1 mm/23° C.). The product was rinsed two times with 2 ml quantities of pentane in which it has a slight solubility and vacuum dried (1 mm/23° C.) to yield 0.0888 g. The quantities of product in the first and second pentane washes were 0.0045 g and 0.0035 g respectively. IR spectra displayed bands characteristic of both the HSCH$_2$CH$_2$CH=CHCH$_2$C(CF$_3$)$_2$(OH) and the HS(CH$_2$)$_5$CH$_3$ ligands, and, from the C—F stretching (1200 cm$^{-1}$) and C—H stretching of the CH$_3$ group, a relative ligand composition of 2:3 HSCH$_2$CH=CHCH$_2$C(CF$_3$)$_2$(OH): HS(CH$_2$)$_5$CH$_3$ was determined for the shell.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A compound having the formula (CF$_3$)$_2$C(OH)-L-M-R, wherein L is unsubstituted or substituted —CH$_2$—CH=CH—;
   wherein M is selected from a substituted or unsubstituted methylene chain, substituted or unsubstituted oxyalkylene chain, and alkyl-substituted or unsubstituted silicon-containing chain, and combinations and multiples thereof;
   wherein R is selected from bromo, —SH, —SZ, and —S—S-M-L-C(CF$_3$)$_2$(OH); and,
   wherein Z represents a thiol protecting group.

2. The compound of claim 1,
   wherein M is selected from —(CH$_2$)$_n$—, —(OCH$_2$CH$_2$)$_m$—, —(Si(CH$_3$)$_2$O)$_p$—Si(CH$_3$)$_2$—(CH$_2$)$_q$—, and combinations thereof, and
   wherein n≥1; m≥1; p≥0; and q≥1.

3. The compound of claim 2, wherein M is —(CH$_2$)$_n$— and R is a thiol.

4. The compound of claim 3, wherein n is 1 or 2.

5. The compound of claim 2, wherein n≤10.

6. The compound of claim 5, wherein n≤5.

7. The compound of claim 2, wherein M is —(OCH$_2$CH$_2$)$_m$—.

8. The compound of claim 7, wherein m≤10.

9. The compound of claim 8, wherein m≤4.

10. The compound of claim 2, wherein M is —(Si(CH$_3$)$_2$O)$_p$—Si(CH$_3$)$_2$—(CH$_2$)$_q$—.

11. The compound of claim 10, wherein p is at least 1.

12. The compound of claim 10, wherein q is at least 3.

13. The compound of claim 1, wherein the compound is selected from
   4-mercapto-2-butenyl-hexafluorodimethylcarbinol; and
   5-mercapto-3-pentenyl-hexafluorodimethylcarbinol.

14. The compound of claim 1, wherein R is bromine.

* * * * *